United States Patent
Sutton et al.

(10) Patent No.: US 9,334,276 B2
(45) Date of Patent: *May 10, 2016

(54) FORMS AND SALTS OF A DIHYDROPYRROLO[1,2C]IMIDAZOLYL ALDOSTERONE SYNTHASE OR AROMATASE INHIBITOR

(71) Applicant: Novartis AG, Basel (CH)

(72) Inventors: Paul Allen Sutton, Parsippany, NJ (US); Eric Loeser, Suffern, NY (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/370,124

(22) PCT Filed: Jan. 15, 2013

(86) PCT No.: PCT/US2013/021521
§ 371 (c)(1),
(2) Date: Jul. 1, 2014

(87) PCT Pub. No.: WO2013/109514
PCT Pub. Date: Jul. 25, 2013

(65) Prior Publication Data
US 2014/0364470 A1    Dec. 11, 2014

Related U.S. Application Data

(60) Provisional application No. 61/587,280, filed on Jan. 17, 2012.

(51) Int. Cl.
*C07D 487/04* (2006.01)

(52) U.S. Cl.
CPC .................... *C07D 487/04* (2013.01)

(58) Field of Classification Search
None
See application file for complete search history.

(56) References Cited

U.S. PATENT DOCUMENTS

| 4,617,307 | A | 10/1986 | Browne | |
|---|---|---|---|---|
| 5,066,656 | A | 11/1991 | Greco et al. | |
| 5,098,911 | A | 3/1992 | Ibrahim | |
| 8,314,097 | B2* | 11/2012 | Ksander et al. | 514/233.2 |
| 8,609,862 | B2* | 12/2013 | Hu et al. | 548/302.7 |
| 8,835,646 | B2 | 9/2014 | Ksander et al. | |
| 2007/0197582 | A1 | 8/2007 | Firooznia | |

FOREIGN PATENT DOCUMENTS

| WO | 9315079 | 8/1993 |
|---|---|---|
| WO | 2007/024945 | 3/2007 |
| WO | 2008076862 | 6/2008 |
| WO | 2011064376 A1 | 6/2011 |
| WO | 2011/088188 | 7/2011 |

OTHER PUBLICATIONS

Chemical Abstracts Registry No. 1315449-72-9, indexed in the Registry file on STN Aug. 9, 2011.*
Hirayama, Reimei et.al.,"Organic Crystal Manufacturing Handbook" Maruzen Publishing Co. pp. 57-59, 2008 (english translation).
Haynes, D.A., et.al.; Occurrence of Pharmaceutically Acceptable Anions and Cations in the Cambridge Structural Database, Journal of Pharmaceutical Sciences, vol. 94(10), pp. 2111-2120, 2005.
Llinás, A. et al. "Polymorphs control: past, present and future" Drug Discovery Today, vol. 13 (5/6), pp. 198-210, 2008.
Correa, C. Guidelines for the examination of pharmaceuticals patents: Developing a public health perspective. World Health Organization (WHO), International Centre for Trade and Sustainable Development (ICTSD) and United Nations Conference on Trade and Development (UNCTAD). Available in Spanish in http://www.ictsd.org/sites/default/files/research/2008/06/correa_guidelines20espanol20final.pdf 2008.
Caira M.R. et al., "Crystalline Polymorphism of Organic Compounds", Topics in current Chemistry; Springer Berlin; vol. 198, pp. 163-208, 1998.
Bomback A.S. Klemmer PJ The incidence and implications of aldosterone breakthrough, Nature clinical practice Nephrology.3(9), pp. 486-492, 2007.
Andersen, Karl et al., The Journal of Clinical Hypertension, vol. 14, No. 9, 2012.
Brittain, Harry G., "Polymorphism in Pharmaceutical Solids", Second Edition, vol. 192, Informa Healthcare., New York, 2009, Table of Contents Only.
Berge et al., "Pharmaceutical Salts", Journal of Pharmaceutical Sciences, 1977, vol. 66, No. 1, pp. 1-19.
Bhattacharya, S., Brittain, H.G., and Suryanarayanan, R., "Thermoanalytical and Crystallographic Methods", in Brittain, H.G. (Ed), Polymorphism in Pharmaceutical Solids, Second Edition, pp. 334 and 335, Informa Healthcare, New York, 2009.

* cited by examiner

Primary Examiner — Laura L. Stockton
(74) Attorney, Agent, or Firm — Michelle Han

(57) ABSTRACT

The invention relates to a phosphate salt or a nitrate salt of 4-(R)-6,7-dihydro-5H-pyrrolo[1,2-c]imidazol-5-yl-3-fluoro-benzonitrile, especially in crystalline form, and specific forms of these salts, as well as related invention embodiments. The salts and salt forms allow for the prophylactic and/or therapeutic treatment of aldosterone synthase and/or aromatase mediated diseases or disorders.

1 Claim, 10 Drawing Sheets

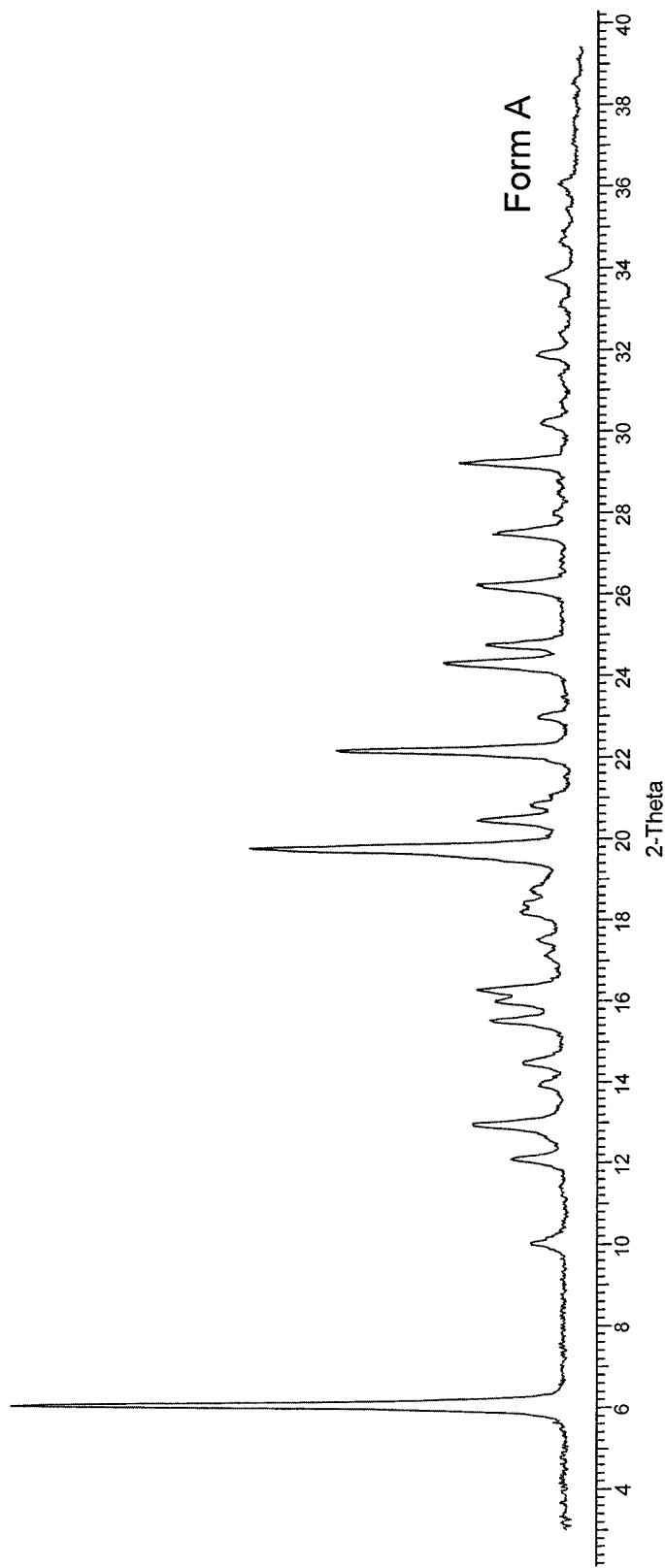
Fig. 1-A

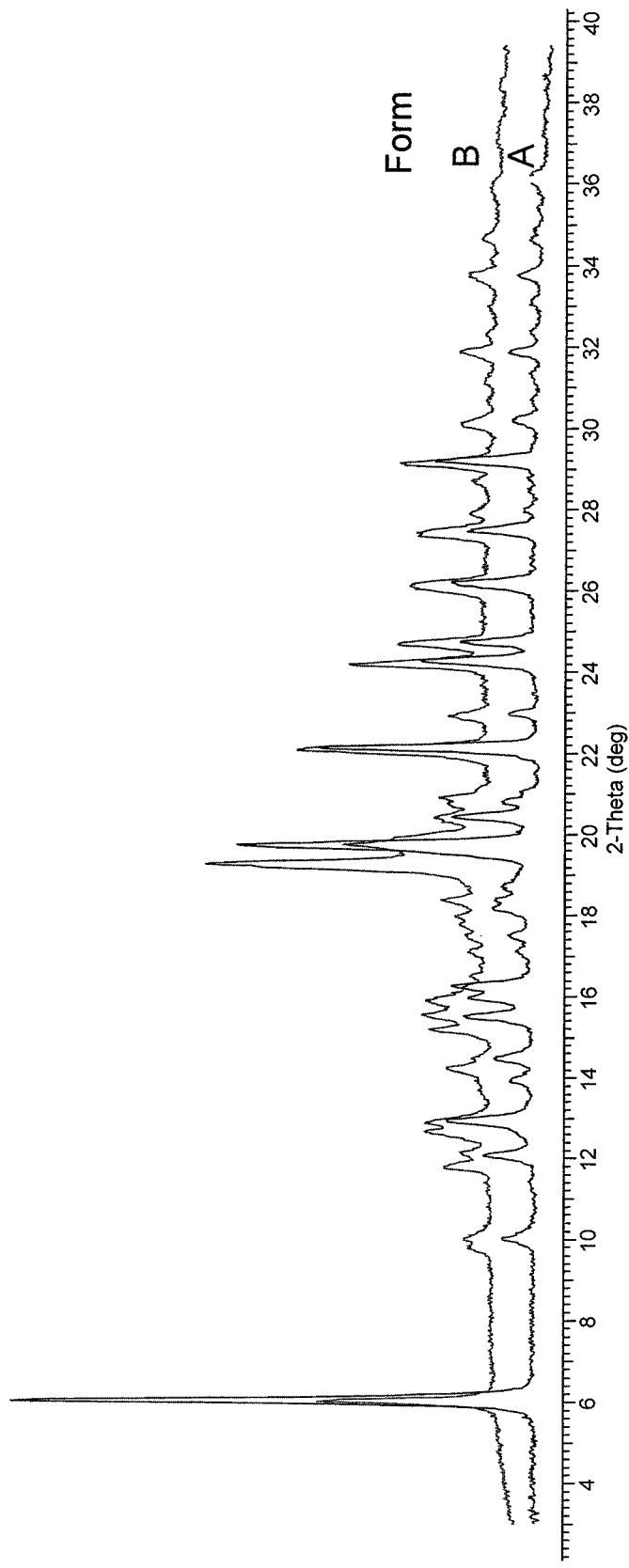
Fig. 1-B

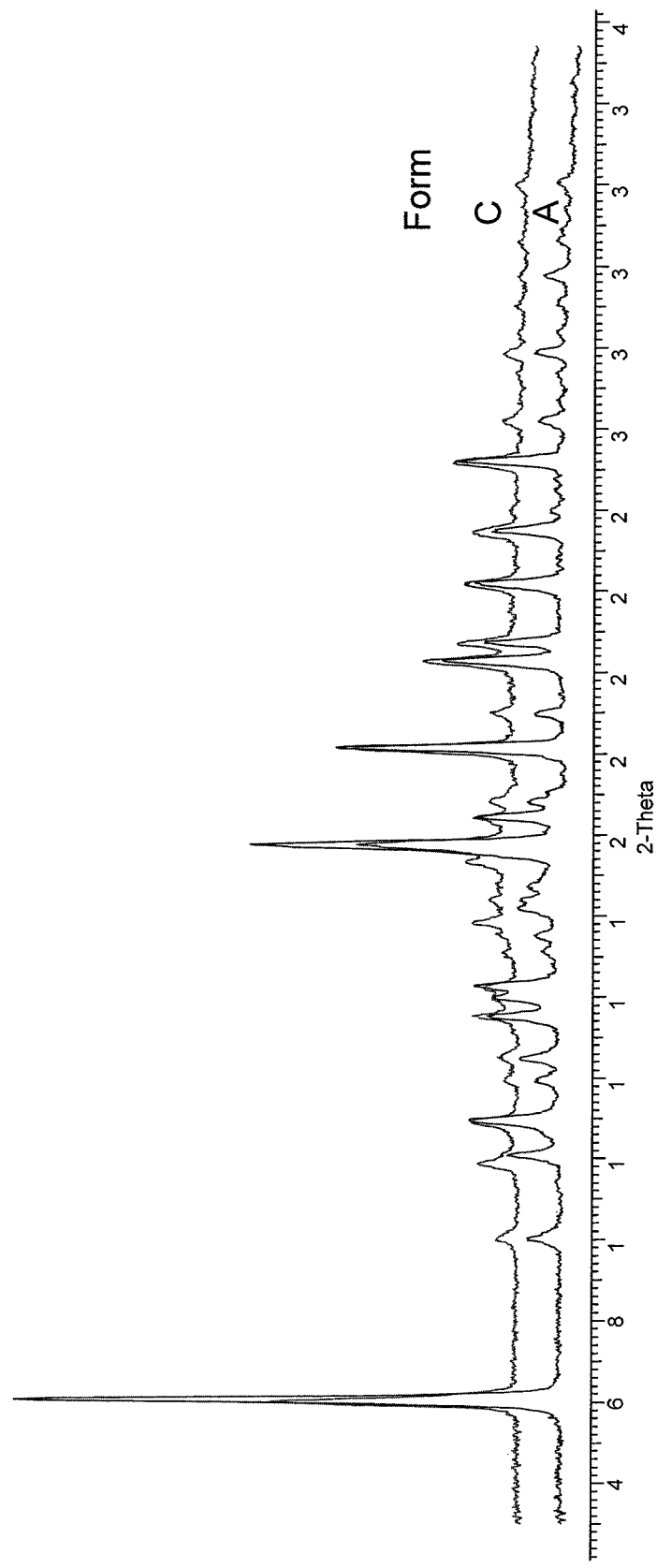
Fig. 1-C

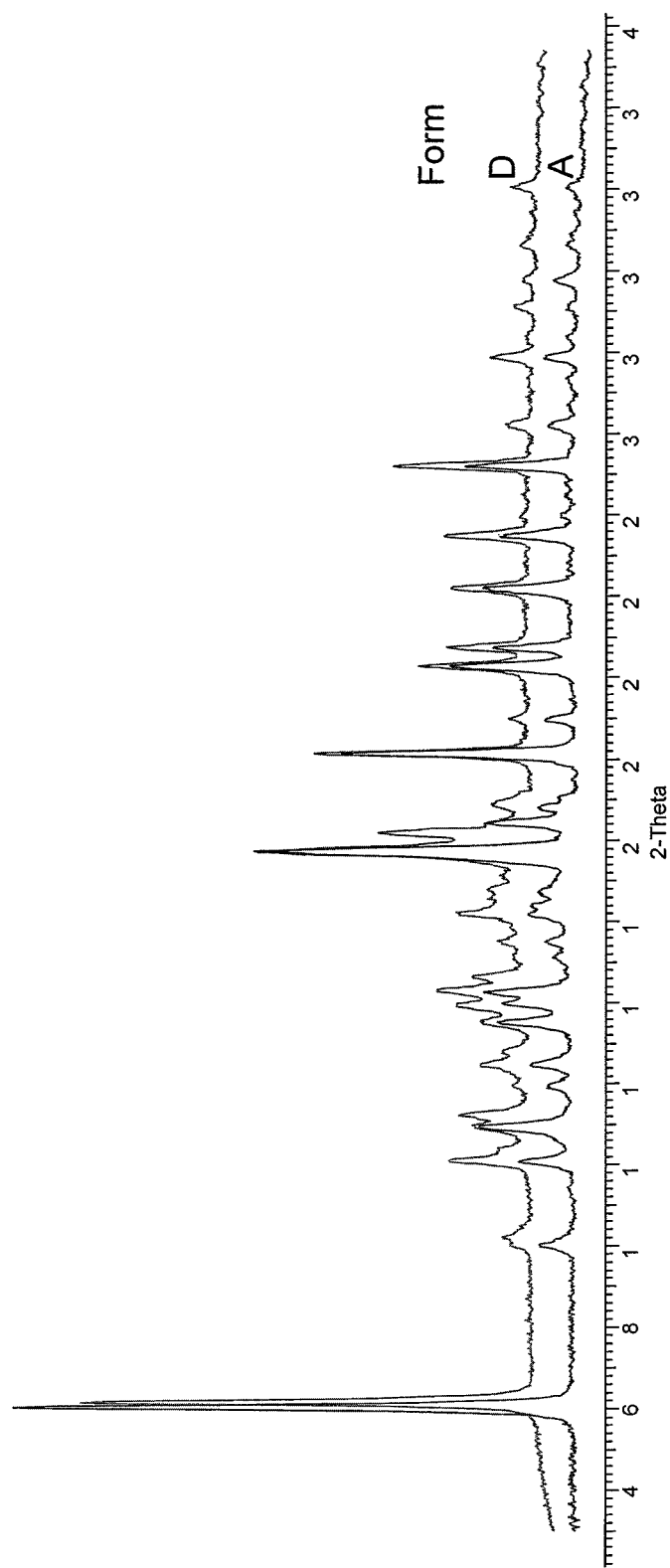
Fig. 1-D

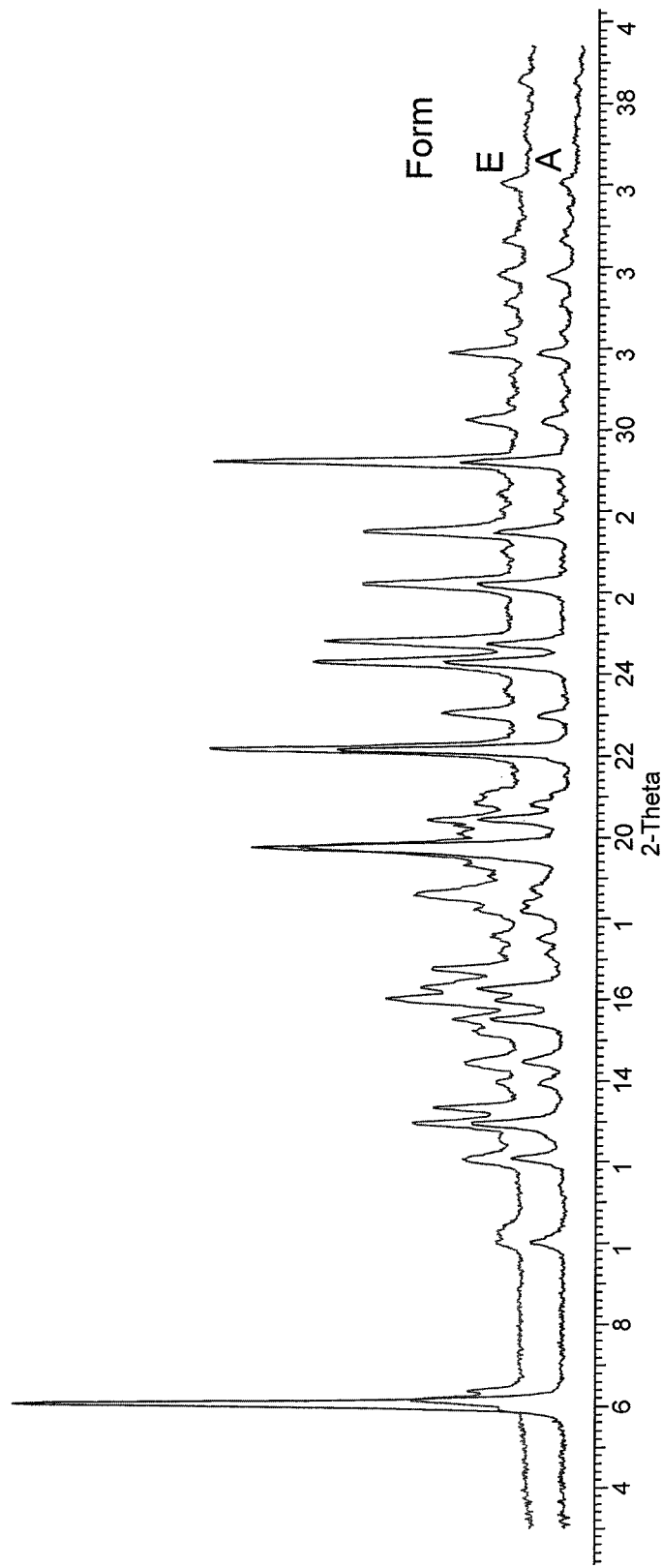
Fig. 1-E

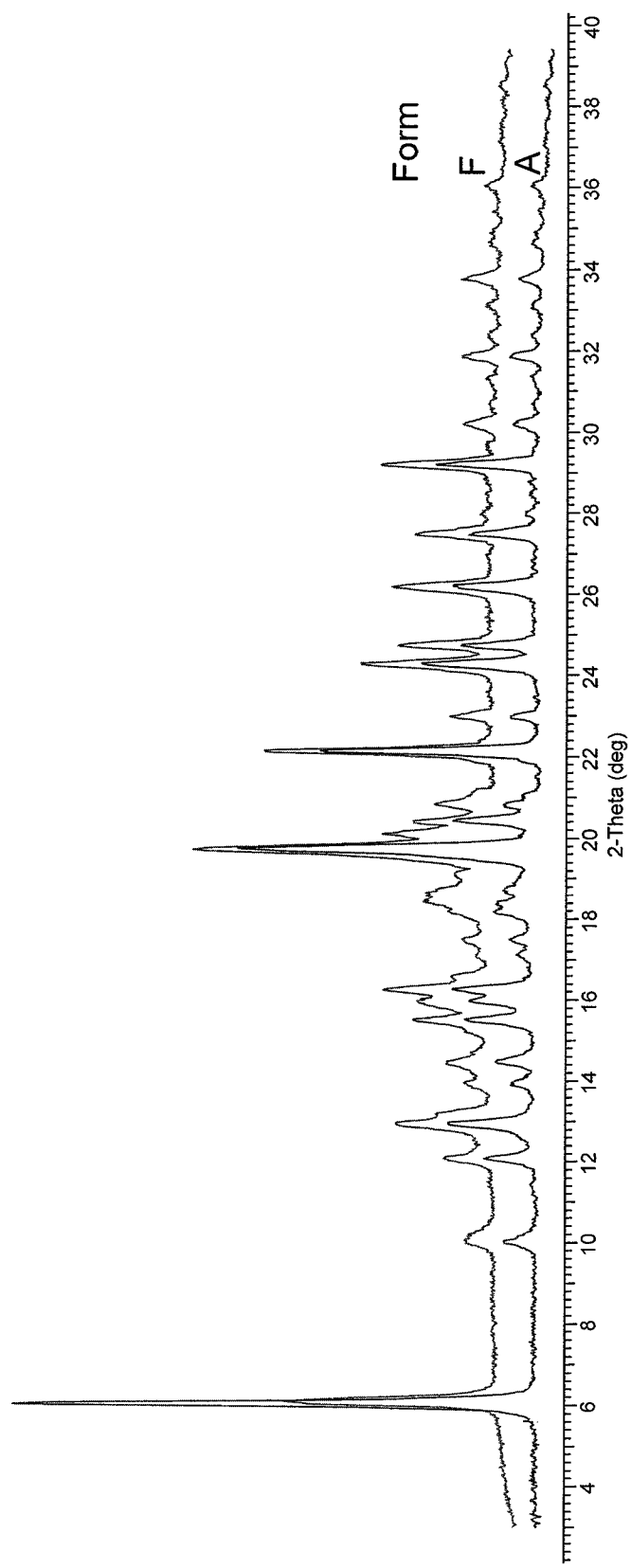
Fig. 1-F

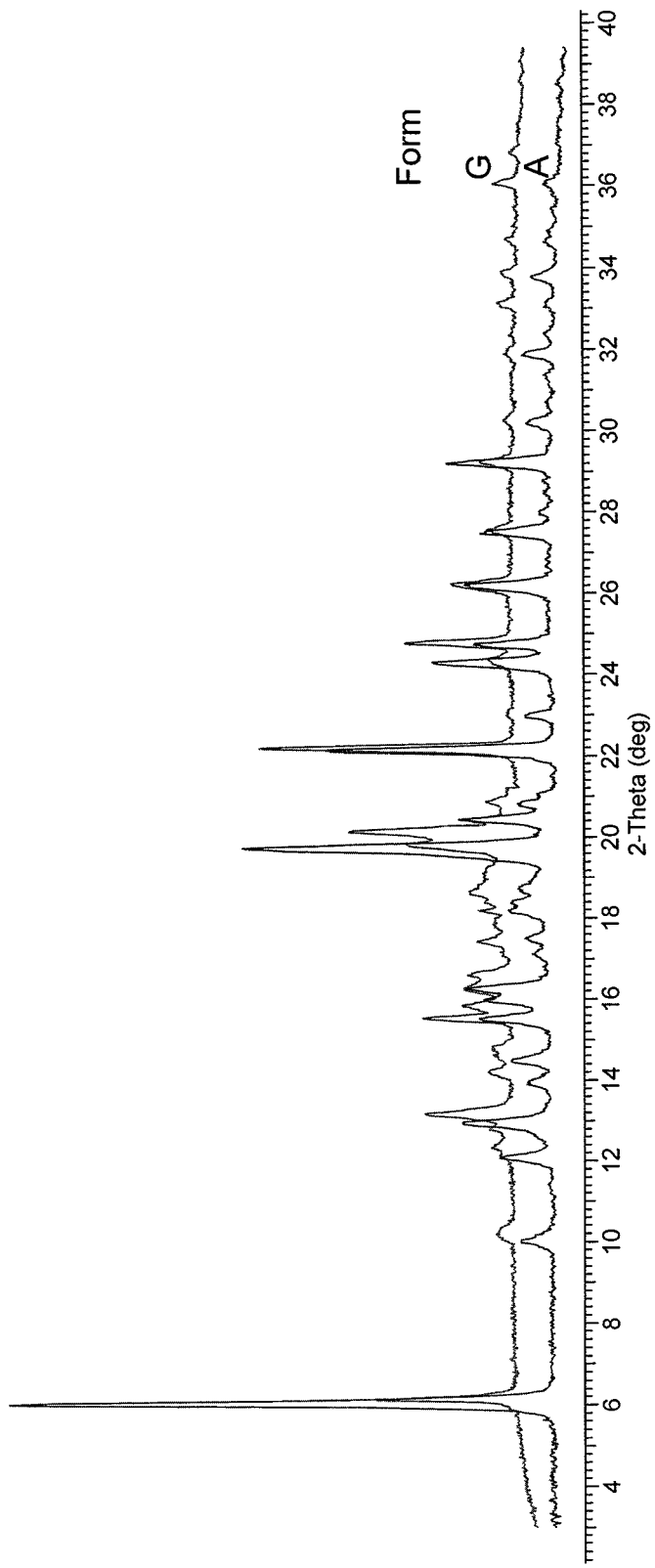
Fig. 1-G

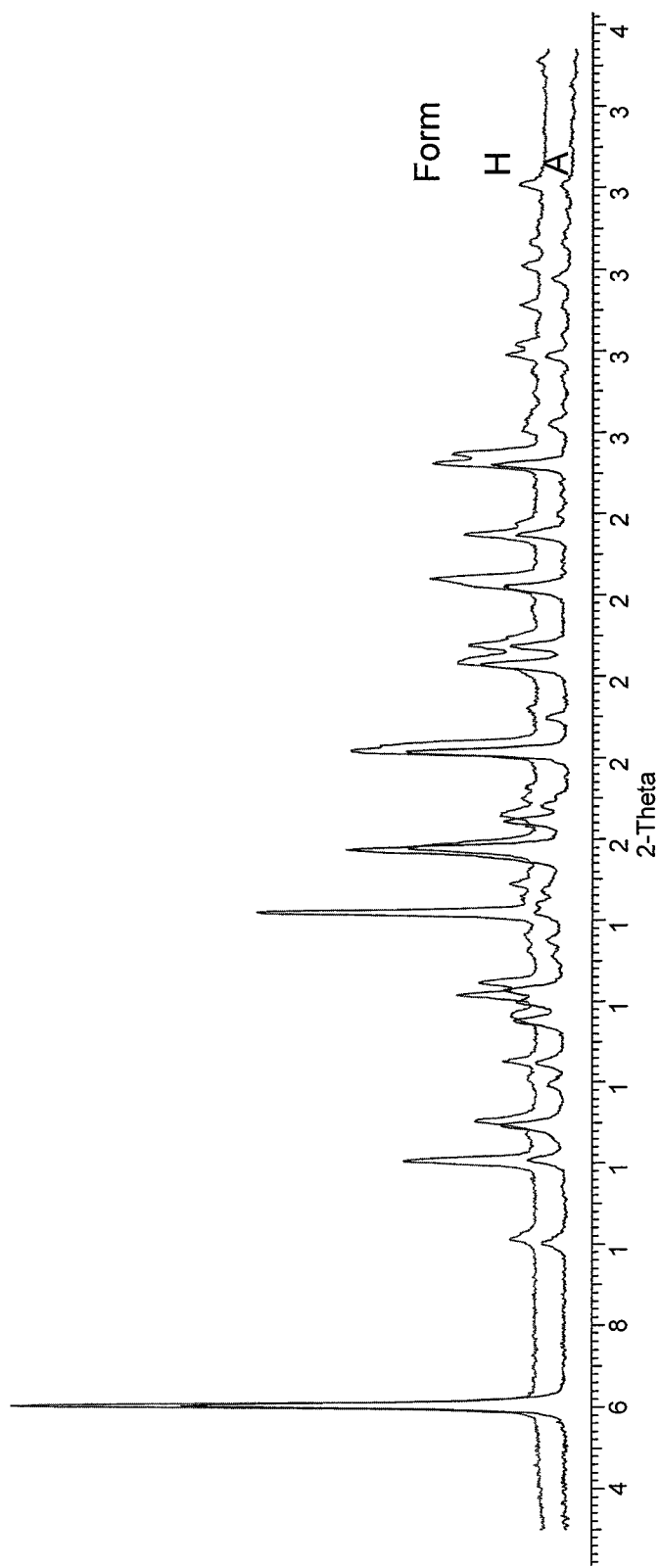
Fig. 1-H

FORMS AND SALTS OF A DIHYDROPYRROLO[1,2C]IMIDAZOLYL ALDOSTERONE SYNTHASE OR AROMATASE INHIBITOR

SUMMARY OF THE INVENTION

The present invention relates to specific salts and salt forms of 4-(R)-(6,7-Dihydro-5H-pyrrolo[1,2-c]imidazol-5-yl)-3-fluoro-benzonitrile (also referred to as "Compound A" within this application), these salts and salt forms for use in methods of treatment of diseases and conditions, the use of these salts and salt forms in the manufacture of medicaments for the treatment of diseases and conditions, methods of treatment comprising administering said salts or salt forms to a mammal in need thereof in therapeutically effective amounts for treating a disease of condition affecting said mammal, pharmaceutical formulations comprising said salts or salt forms.

BACKGROUND OF THE INVENTION

The compound 6,7-dihydro-5H-pyrrolo[1,2-c]imidazol-5-yl-3-fluoro-benzonitrile, its 4-(R)-enantiomer with formula (I)

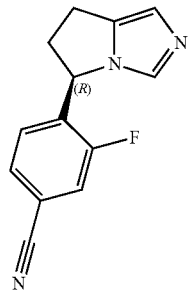

and its manufacture are described in WO 2007/024945 A1, among many other compounds disclosed therein. It is known to be active as inhibitor of aldosterone synthase and aromatase.

For example, in a clinical proof-of-concept study in patients with primary aldosteronism efficiency of 4-(R)-(6,7-Dihydro-5H-pyrrolo[1,2-c]imidazol-5-yl)-3-fluoro-benzonitrile free base in inhibition of aldosterone synthase could be shown (see e.g. Amar L. et al., Hypertension 56(5), 831-838 November 2010 (Epub 2010 September).

No specific salts of the compounds mentioned in said patent application are disclosed.

Compound A in the form of free base has a quite low melting point of about 111.5° C. which constitutes a certain risk regarding physical stability of the compound during manufacture, storage and processing to pharmaceutical formulations. Thus there was a need to find specific processing conditions or specific forms of this compound that allow for stable processing.

GENERAL DESCRIPTION OF THE INVENTION

Surprisingly it was difficult to obtain salt of Compound A. About 20 various different salt forming agents were evaluated with Compound A, but only 3 salts were formed: phosphate salt, nitrate salt and hydrochloride salt. Other salt forming agents did not produce solid material at all or not in any useful quantity or quality.

The phosphate salt shows the most superior properties. It can be isolated and manufactured better and thus is advantageous over the free base compound, with additional properties such as a higher melting point over the free base and other salts, lower hygroscopicity and improved aqueous solubility. The nitrate salt also shows comparable advantages.

DETAILED DESCRIPTION OF THE INVENTION

The invention, in a first aspect, relates to a phosphate salt of Compound A, especially in crystalline forms, particularly in crystalline Form A as described below.

The term "phosphate salt" as used in the present application, refers to the acid addition salt of compound A with phosphoric acid. More particularly, it refers to the dihydrogen-phosphate of compound A protonated once, that is, wherein compound A is protonated once and thus each molecule carries a single positive charge, while the counterion is $H_2PO_4^-$).

The second aspect of the invention relates to a nitrate salt of Compound A, especially in crystalline forms.

In further aspects the invention relates to the salts or salt forms mentioned herein in the manufacture of medicaments for the treatment of diseases and conditions, to said salts or salt forms (especially in the form of pharmaceutical compositions) for use in the treatment of diseases and conditions, to methods of treatment comprising administering said salts or salt forms to a mammal in need thereof in therapeutically effective amounts for treating a disease of condition affecting said mammal, pharmaceutical formulations comprising said salts or salt forms.

Thus, in one further aspect the invention relates to a pharmaceutical composition that includes (an especially prophylactically or therapeutically effective amount of) a phosphate salt of Compound A and one or more pharmaceutically acceptable excipients, in particular for use in the treatment of conditions or diseases described herein, especially conditions or diseases mediated by aldosterone synthase or aromatase. The pharmaceutical compositions of this aspect of the invention may be formulated, e.g., for oral administration.

In accordance with yet another aspect, the invention provides a process for making a nitrate salt or a phosphate salt, especially in crystalline form, respectively, of Compound A, the process comprising:
 (a) providing a solution of Compound A in either a protic or an aprotic polar solvent, especially in an aqueous-alcoholic or alcoholic solution (alcoholic especially referring to hydroxy-$C_{1-7}$alkanes) (where said solution may have a temperature in the range e.g. from 0° C. to the boiling point of the solution, e.g. up to 90° C., e.g. in the range from 10 to 50° C.);
 (b) adding nitric acid or phosphoric acid; and
 (c) isolating the formed crystalline form of a nitrate salt or a phosphate salt of Compound A;
 where if desired one obtainable (then educt) salt can be converted into the other salt by addition of the corresponding acid contributing the other anion to a solution of the educt salt.

Variants of this process are provided and included as embodiments of the invention, e.g. in which seed crystals of the respective nitrate salt or phosphate salt of Compound A are added, the solvent is at least partially removed (e.g. by evaporation), the temperature is lowered to improve crystallization or on which anti-solvents are added to improve precipitation, or any combinations of such process measures.

This process may also be a step (e.g. the final purification step) in the manufacture of the respective salt, e.g. at the end of the process described for the manufacture of the free base in WO 2007/024945 A1, and the corresponding general method of manufacture is incorporated by reference herein and applied specifically to the preparation of the compound Compound A.

Forms B, C, D, E, F, G and H of the phosphate salt may be obtained e.g. as described in the Examples, where the temperature is room temperature (23° C.)±10° C. and the solvents may be replaced by corresponding solvents.

In one first particular embodiment, the invention relates to a phosphate salt of Compound A, in particular with a molar ratio of Compound A to phosphate of about 1:1, in particular in crystalline form.

In one special embodiment, the invention relates to a crystalline phosphate salt of Compound A having a melting point that is at least 50° C., at least 55° C. or at least 85° C. higher than that of the free base.

In one embodiment, the phosphate salt of Compound A has a melting temperature of at least 170° C. or at least 197° C.

In one embodiment, the phosphate salt of Compound A has a melting temperature between 205° C. to 214° C., between 206° C. to 213° C., between 208° C. to 213° C., between 209° C. to 212° C. or between 209° C. to 211° C.

The melting temperatures herein, if not described otherwise, are obtained using thermogravimetry/differential thermal analysis (TG/DTA). TG/DTA is determined using a Seiko EXSTAR TG/DTA 6000, temperature range room temperature to 250° C., scan rate 10° C./min, nitrogen flow 100 ml/min.

In another special embodiment, the invention relates to "Form A" of the crystalline phosphate salt of Compound A, especially with an XRPD showing at least one, more preferably two, three, four, five, six, seven, eight, nine, ten, 11, 12, 13, 14, 15, 16 or all of the following peaks, given as angle of refraction 2-theta (θ) values, obtainable as described in the Examples, where each peak may vary by ±1 or ±0.5, in particular ±0.2 degrees: 6.0, 10.0, 12.1, 12.9, 14.0, 14.5, 15.5, 16.0, 16.3, 17.5, 18.2, 18.4, 19.7, 20.4, 22.1, 24.3, 29.2, with the underlined peaks defining a preferred embodiment and all peaks defining a more preferred embodiment.

In one embodiment, the "Form A" of the crystalline phosphate salt of Compound A has a melting temperature of 210±5° C., 210±2° C., 210±1° C. or 210±0.5° C. or 210.2° C.

In one embodiment, the invention relates to Form A with an XRPD showing at least one, more preferably two, three, four, five, six, seven, eight or all of the following peaks, given as angle of refraction 2-theta (θ) values, obtainable as described in the Examples, where each peak may vary by ±1 or ±0.5, in particular ±0.2 degrees: 6.0, 12.9, 15.5, 16.0, 16.3, 19.7, 20.4, 22.1, 24.3, 29.2.

In one embodiment, the two largest peaks of Form A in the XRPD diagram have a relative intensity of 1 to 0.5 to 0.7, especially of 1 to 0.55 to 0.65, more especially of 0.57 to 0.61, e.g. of 1 to 0.59 (obtainable by integration of each of the peaks in the XRPD diagrams). In a particular embodiment the larger peak is at a 2-theta (θ) value of 6.0±1 or ±0.5, in particular ±0.2 degrees and the smaller peak at a 2-theta (θ) value of 19.7±1 or ±0.5, in particular ±0.2 degrees, respectively.

Another embodiment relates to form A with an XRPD showing at least one or all of the following peaks, given as angle of refraction 2-theta (θ) values, obtainable as described in the Examples, where each peak may vary by ±1 or ±0.5, in particular ±0.2 degrees: 12.9 16.3 and 20.4 degrees.

Preferred is the phosphate salt showing an XRPD as shown in FIG. 1-A.

A specific embodiment of the invention relates to "Form A" of the crystalline phosphate salt of Compound A, having a melting point between 209 and 212° C.

In one embodiment, the invention relates to a "Form B" of crystalline phosphate salt of Compound A with an XRPD showing at least one, more preferably two, three, four, five, six, seven, eight, nine, ten, 11, 12, 13, 14, 15, 16, 17, 18 or all of the following peaks, given as angle of refraction 2-theta (θ) values, obtainable as described in the Examples, where each peak may vary by ±1 or ±0.5, in particular ±0.2 degrees: 6.0, 9.8, 11.8, 12.7, 12.9, 14.0, 14.3, 15.2, 16.0, 16.3, 17.5, 18.0, 18.4, 19.3, 19.7, 20.1, 22.1, 24.3, 29.2, with the underlined peaks defining a preferred embodiment, all peaks defining a more preferred embodiment. More preferred is the crystalline phosphate salt Form B showing an XRPD as shown in FIG. 1-B.

An embodiment of the invention relates to "Form B" of the crystalline phosphate salt of Compound A, having a melting point of 209±5° C., for example between 207 and 211° C., e.g. of 209.0° C.

In one embodiment, the invention relates to a "Form C" of crystalline phosphate salt of Compound A with an XRPD showing at least one, more preferably two, three, four, five, six, seven, eight, nine, ten, 11, 12, 13, 14, 15, 16, 17 or all of the following peaks, given as angle of refraction 2-theta (θ) values, obtainable as described in the Examples, where each peak may vary by ±1 or ±0.5, in particular ±0.2 degrees: 6.0, 10.0, 11.9, 12.9, 14.0, 14.5, 15.5, 16.0, 16.3, 17.8, 18.2, 18.4, 19.3, 19.7, 20.1, 22.1, 24.3, 29.2, with the underlined peaks defining a preferred embodiment, all peaks defining a more preferred embodiment. More preferred is the crystalline phosphate salt Form C showing an XRPD as shown in FIG. 1-C.

An embodiment of the invention relates to "Form C" of the crystalline phosphate salt of Compound A, having a melting point of 191±5° C., for example between 189 and 193° C., e.g. of 190.7° C.

In one embodiment, the invention relates to a "Form D" of crystalline phosphate salt of Compound A, with an XRPD showing at least one, more preferably two, three, four, five, six, seven, eight, nine, ten, 11, 12, 13, 14, 15, 16, 17 or all of the following peaks, given as angle of refraction 2-theta (θ) values, obtainable as described in the Examples, where each peak may vary by ±1 or ±0.5, in particular ±0.2 degrees: 6.2, 10.0, 12.4, 12.9, 13.3, 14.8, 15.5, 16.0, 16.6, 17.5, 18.2, 18.4, 19.3, 19.7, 20.2, 22.1, 24.3, 29.2, with the underlined peaks defining a preferred embodiment, all peaks defining a more preferred embodiment. More preferred is the crystalline phosphate salt Form D showing an XRPD as shown in FIG. 1-D.

An embodiment of the invention relates to "Form D" of the crystalline phosphate salt of Compound A, having a melting point of 211±5° C., for example between 208 and 213° C., e.g. of 210.8° C.

In one embodiment, the invention relates to a "Form E" of crystalline phosphate salt of Compound A, with an XRPD showing at least one, more preferably two, three, four, five, six, seven, eight, nine, ten, 11, 12, 13, 14, 15, 16, 17 or all of the following peaks, given as angle of refraction 2-theta (θ) values, obtainable as described in the Examples, where each peak may vary by ±1 or ±0.5, in particular ±0.2 degrees: 6.4, 10.3, 12.1, 12.9, 13.3, 14.5, 15.2, 16.0, 16.8, 17.5, 18.2, 18.4, 19.3, 19.7, 20.1, 22.1, 24.3, 29.2, with the underlined peaks defining a preferred embodiment, all peaks defining a more preferred embodiment. More preferred is the crystalline phosphate salt Form E showing an XRPD as shown in FIG. 1-E.

An embodiment of the invention relates to "Form E" of the crystalline phosphate salt of Compound A, having a melting point of 214±5° C., for example between 211 and 216° C., e.g. of 213.6° C.

In one embodiment, the invention relates to a "Form F" of crystalline phosphate salt of Compound A, with an XRPD showing at least one, more preferably two, three, four, five, six, seven, eight, nine, ten, 11, 12, 13, 14, 15, 16, 17 or all of the following peaks, given as angle of refraction 2-theta (θ) values, obtainable as described in the Examples, where each peak may vary by ±1 or ±0.5, in particular ±0.2 degrees: 6.0, 10.0, 12.1, 12.9, 13.8, 14.0, 15.5, 16.0, 16.6, 17.5, 18.2, 18.4, 19.1, 19.7, 20.1, 22.1, 24.3, 29.2, with the underlined peaks defining a preferred embodiment, all peaks defining a more preferred embodiment. More preferred is the crystalline phosphate salt Form F showing an XRPD as shown in FIG. 1-F.

An embodiment of the invention relates to "Form F" of the crystalline phosphate salt of Compound A, having a melting point of 201±5° C., for example between 199 and 203° C., e.g. of 201.1° C.

In one embodiment, the invention relates to a "Form G" of crystalline phosphate salt of Compound A, with an XRPD showing at least one, more preferably two, three, four, five, six, seven, eight, nine, ten, 11, 12, 13, 14, 15, 16, or all of the following peaks, given as angle of refraction 2-theta (θ) values, obtainable as described in the Examples, where each peak may vary by ±1 or ±0.5, in particular ±0.2 degrees: 6.0, 12.1, 13.1, 14.0, 14.5, 15.5, 15.8, 16.3, 17.5, 18.2, 18.4, 19.3, 19.7, 20.1, 22.1, 24.3, 29.2, with the underlined peaks defining a preferred embodiment, all peaks defining a more preferred embodiment. More preferred is the crystalline phosphate salt Form G showing an XRPD as shown in FIG. 1-G.

An embodiment of the invention relates to "Form G" of the crystalline phosphate salt of Compound A, having a melting point of 180±5° C., for example between 177 and 183° C., e.g. of 179.8° C.

In one embodiment, the invention relates to a "Form H" of crystalline phosphate salt of Compound A, with an XRPD showing at least one, more preferably two, three, four, five, six, seven, eight, nine, ten, 11, 12, 13, 14, 15, 16, or all of the following peaks, given as angle of refraction 2-theta (θ) values, obtainable as described in the Examples, where each peak may vary by ±1 or ±0.5, in particular ±0.2 degrees: 6.0, 10.2, 12.1, 13.1, 14.0, 14.5, 15.5, 16.2, 16.5, 17.5, 18.2, 18.4, 19.3, 19.7, 20.1, 22.2, 24.3, 29.5, with the underlined peaks defining a preferred embodiment, all peaks defining a more preferred embodiment. More preferred is the crystalline phosphate salt Form H showing an XRPD as shown in FIG. 1-H.

An embodiment of the invention relates to "Form H" of the crystalline phosphate salt of Compound A, having a melting point of 208±5° C., for example between 206 and 210° C., e.g. of 208.0° C.

In one embodiment, the invention relates to a nitrate salt of Compound A, in particular with a molar ratio of Compound A to nitrate of about 1:1, in particular in crystalline form.

In one special embodiment, the invention relates to a crystalline nitrate salt of Compound A having a melting point that is at least 40° C. higher than that of the free base, especially (using TG/DTA as described above) between 160 and 163° C.

In another special embodiment, the invention relates to a crystalline nitrate salt of Compound A, with an XRPD showing at least one, more preferably two, three, four, five, six, seven, eight, nine, ten, 11, 12, 13, 14, 15, 16, 17 or all of the following peaks, given as angle of refraction 2-theta (θ) values, obtainable as described in the Examples, where each peak may vary by ±1 or ±0.5, in particular ±0.2 degrees: 7.4, 10.6, 12.5, 15.0, 15.7, 17.5, 18.0, 18.7, 20.4, 21.2, 22.8, 24.6, 26.5, 28.2, 28.8, 29.9, 31.0, 31.5, with the underlined peaks defining a preferred embodiment, all peaks defining a more preferred embodiment. Preferred is the nitrate salt showing an XRPD as shown in FIG. 2.

A specific embodiment of the invention relates to a crystalline nitrate salt of Compound A showing the XRPD characteristics above and a melting point between 160 and 163° C. using TG/DTA.

The compound 6,7-dihydro-5H-pyrrolo[1,2-c]imidazol-5-yl-3-fluoro-benzonitrile as free base) and especially its enantiomers, especially 4-(R)-(6,7-dihydro-5H-pyrrolo[1,2-c]imidazol-5-yl)-3-fluoro-benzonitrile, can be manufactured as described in published international patent application WO 2007/024945 which is incorporated by reference herein (see especially Table 2, and Chiral Resolution on page 87, F. 5).

"About" where used means especially ±10%, ±5% or ±3% (referring to the given numeric value, respectively), if not indicated otherwise. In each of the invention embodiments, "about" can be deleted.

"Prophylactically or therapeutically effective amount" means the amount of a compound that, when administered for treating or preventing a disease or disorder mentioned above or below, is sufficient to effect such treatment or prevention for the disease or disorder, prophylactic especially refers to the prevention of the onset or recurrence or ameliorating the onset or recurrence of such disease or disorder, therapeutic especially refers to the amelioration or complete suppression of one or more symptoms up to the cure of such disease or disorder. The "prophylactically or therapeutically effective amount" will vary depending on the salt(s) or salt form(s) used, the disease or disorder and its severity and the age, weight, etc., of the patient to be treated.

The term "pharmaceutical composition" is intended to encompass a product comprising the active ingredient(s), optionally at least one pharmaceutically acceptable excipients. The pharmaceutical compositions of the present invention encompass any composition made by admixing the active ingredient, additional active ingredient(s) and pharmaceutically acceptable excipients.

The term "pharmaceutical composition" is also intended to comprise a combination product, comprising a salt or salt form according to claim 1 in combination with one or more other therapeutic agents (pharmaceutically active compounds) and preferably at least one pharmaceutically acceptable excipient.

Other therapeutic agents include at least one or two or more selected from the following groups:
 (i) angiotensin II receptor antagonist or a pharmaceutically acceptable salt thereof,
 (ii) HMG-Co-A reductase inhibitor or a pharmaceutically acceptable salt thereof,
 (iii) angiotensin converting enzyme (ACE) Inhibitor or a pharmaceutically acceptable salt thereof,
 (iv) calcium channel blocker (CCB) or a pharmaceutically acceptable salt thereof,
 (v) dual angiotensin converting enzyme/neutral endopeptidase (ACE/NEP) inhibitor or a pharmaceutically acceptable salt thereof,
 (vi) endothelin antagonist or a pharmaceutically acceptable salt thereof,
 (vii) renin inhibitor or a pharmaceutically acceptable salt thereof,
 (viii) diuretic or a pharmaceutically acceptable salt thereof,
 (ix) an ApoA-I mimic;
 (x) an anti-diabetic agent;

(xi) an obesity-reducing agent;
(xii) an aldosterone receptor blocker,
(xiii) an endothelin receptor blocker,
(xiv) a CETP inhibitor,
(xv) an inhibitor of Na—K-ATPase membrane pump;
(xvi) a beta-adrenergic receptor blocker or an alpha-adrenergic receptor blocker;
(xvii) a neutral endopeptidase (NEP) inhibitor; and
(xviii) an inotropic agent.

Such compounds are e.g. defined in WO 2007/024945 A1 and are included here by reference.

Also where not specifically mentioned, the therapeutic agent(s) may be in the free (non-salt) form or in the form of a pharmaceutically acceptable salt, respectively.

A compound of the present invention may be administered either simultaneously, before or after the other therapeutic agent (active ingredient), either separately by the same or different route of administration or together in the same pharmaceutical formulation.

Thus the combination product may comprise the salt or salt form according to the invention in one, one or more other therapeutic agents in a separate formulation, but in the form of a kit of parts for the simultaneous or chronically staggered administration, or in one fixed combination.

Thus, the combinations as described above can be administered to a subject via simultaneous, separate or sequential administration (use). Simultaneous administration (use) can take place in the form of one fixed combination with two or three or more active ingredients, or by simultaneously administering two or three or more compounds that are formulated independently. Sequential administration (use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism).

Separate administration (use) preferably means administration of the compounds or active ingredients of the combination independently of each other at different time points, preferably meaning that two, or three or more compounds are administered such that no overlap of measurable blood levels of both compounds are present in an overlapping manner (at the same time).

Also combinations of two or three or more of sequential, separate and simultaneous administrations are possible, preferably such that the combination compound-drugs show a joint therapeutic effect that exceeds the effect found when the combination compound-drugs are used independently at time intervals so large that no mutual effect on their therapeutic efficiency can be found, a synergistic effect being especially preferred.

Alternatively, the pharmaceutical compositions contain a therapeutically effective amount of a salt or salt form of Compound A of the invention as defined above or below, either alone or in a combination with one or more therapeutic agents, e.g., each at an effective therapeutic dose as reported in the art, selected from the group consisting of an antiestrogen; an anti-androgen; a gonadorelin agonist; a topoisomerase I inhibitor, a topoisomerase II inhibitor; a microtubule active agent; an alkylating agent; an anti-neoplastic antimetabolite; a platin compound; a compound targeting/decreasing a protein or lipid kinase activity or a protein or lipid phosphatase activity, a anti-angiogenic compound; a compound which induces cell differentiation processes; monoclonal antibodies; a cyclooxygenase inhibitor; a bisphosphonate; a heparanase inhibitor; a biological response modifier, an inhibitor of Ras oncogenic isoforms; a telomerase inhibitor; a protease inhibitor, a matrix metalloproteinase inhibitor, a methionine aminopeptidase inhibitor; a proteasome inhibitor; agents which target, decrease or inhibit the activity of Flt-3; an HSP90 inhibitor; antiproliferative antibodies; an HDAC inhibitor, a compound which targets, decreases or inhibits the activity/function of serine/threonine mTOR kinase; a somatostatin receptor antagonist; an anti-leukemic compound; tumor cell damaging approaches; an EDG binder; a ribonucleotide reductase inhibitor, an S-adenosylmethionine decarboxylase inhibitor; a monoclonal antibody of VEGF or VEGFR; photodynamic therapy; an Angiostatic steroid; an implant containing corticosteroids; an AT1 receptor antagonist; and an ACE inhibitor.

Additionally, the present invention provides:
a pharmaceutical composition or combination of the present invention for use as a medicament;
the use of a pharmaceutical composition or combination of the present invention for the delay of progression and/or treatment of a disorder or disease mediated by aldosterone synthase, or responsive to inhibition of aldosterone synthase, or characterized by abnormal activity or expression of aldosterone synthase.
the use of a pharmaceutical composition or combination of the present invention for the delay of progression and/or treatment of a disorder or disease mediated by aromatase, or responsive to inhibition of aromatase, or characterized by abnormal activity or expression of aromatase.
the use of a pharmaceutical composition or combination of the present invention for the delay of progression and/or treatment of a disorder or disease selected from hypokalemia, hypertension, congestive heart failure, atrial fibrillation, renal failure, in particular, chronic renal failure, restenosis, sleep apnoea, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction.

The salt(s) or salt form(s) of the present invention are useful as aldosterone synthase inhibitors (see e.g. WO 2007/024945 incorporated by reference herein regarding the diseases and disorders related to aldosterone synthase). In particular, the salt(s) or salt form(s) of the present invention as aldosterone synthase inhibitors are useful for treatment of a disorder or disease characterized by abnormal aldosterone synthase activity. Preferably, the salt(s) or salt form(s) of the present invention are also useful for treatment of a disorder or disease selected from hypokalemia, hypertension, congestive heart failure, atrial fibrillation, renal failure, in particular, chronic renal failure, restenosis, sleep apnoea, atherosclerosis, syndrome X, obesity, nephropathy, post-myocardial infarction, coronary heart diseases, inflammation, increased formation of collagen, fibrosis such as cardiac or myocardiac fibrosis and remodeling following hypertension and endothelial dysfunction.

The disorder or disease to be treated with a salt or salt form according to the inventions is especially selected from hypertension (essential or resistant), primary aldosteronism congestive heart failure and acute heart failure.

Further diseases or disorders of specific interest are selected from the group consisting of heart failure, cachexia, acute coronary syndrome, chronic stress syndrome, Cushing's disease, Cushing's syndrome, metabolic syndrome or hypercortisolemia. In a very preferred embodiment the disease is Cushing's disease "Protic or an aprotic solvents" may be selected from aqueous or non-aqueous solvents or solvent mixtures, e.g. comprising one or more selected from water, $C_{1-7}$alkanols, $C_{1-8}$ketones, $C_{1-7}$alkanediols, $C_{1-7}$alkylnitriles, $C_{1-7}$alkyl-$C_{2-7}$alkanoates, with methanol, acetone, propylene glycol, ethyl acetate, or especially ethanol being especially preferred.

"Anti-solvent" is a solvent which when added to an existing solution of a substance reduces the solubility of the substance. In the case of the present salts, anti-solvents are especially less polar (more hydrophilic) solvents than those used for dissolving Compound A before the addition of nitric acid or phosphoric acid, e.g. organic solvents that are at least to a certain extent (e.g. at least up to 10 vol %) miscible with water.

Throughout this specification, where the plural forms "salts" or "salt forms" are used, this also includes a single salt or a single salt form.

DESCRIPTION OF THE FIGURES

The Figures show the XRDP of the following salts and salt forms of Compound A:

FIG. 1-A shows the X-ray powder diffraction pattern of the initial phosphate salt Form A.

FIG. 1-B shows the X-ray powder diffraction patter of phosphate salt Form B.

FIG. 1-C shows the X-ray powder diffraction pattern of phosphate salt Form C.

FIG. 1-D shows the X-ray powder diffraction patter of phosphate salt Form D.

FIG. 1-E shows the X-ray powder diffraction patter of phosphate salt Form E.

FIG. 1-F shows the X-ray powder diffraction pattern of phosphate salt Form F.

FIG. 1-G shows the X-ray powder diffraction pattern of phosphate salt Form G.

FIG. 1-H shows the X-ray powder diffraction pattern of phosphate salt Form H.

EXAMPLES

Figure 2:
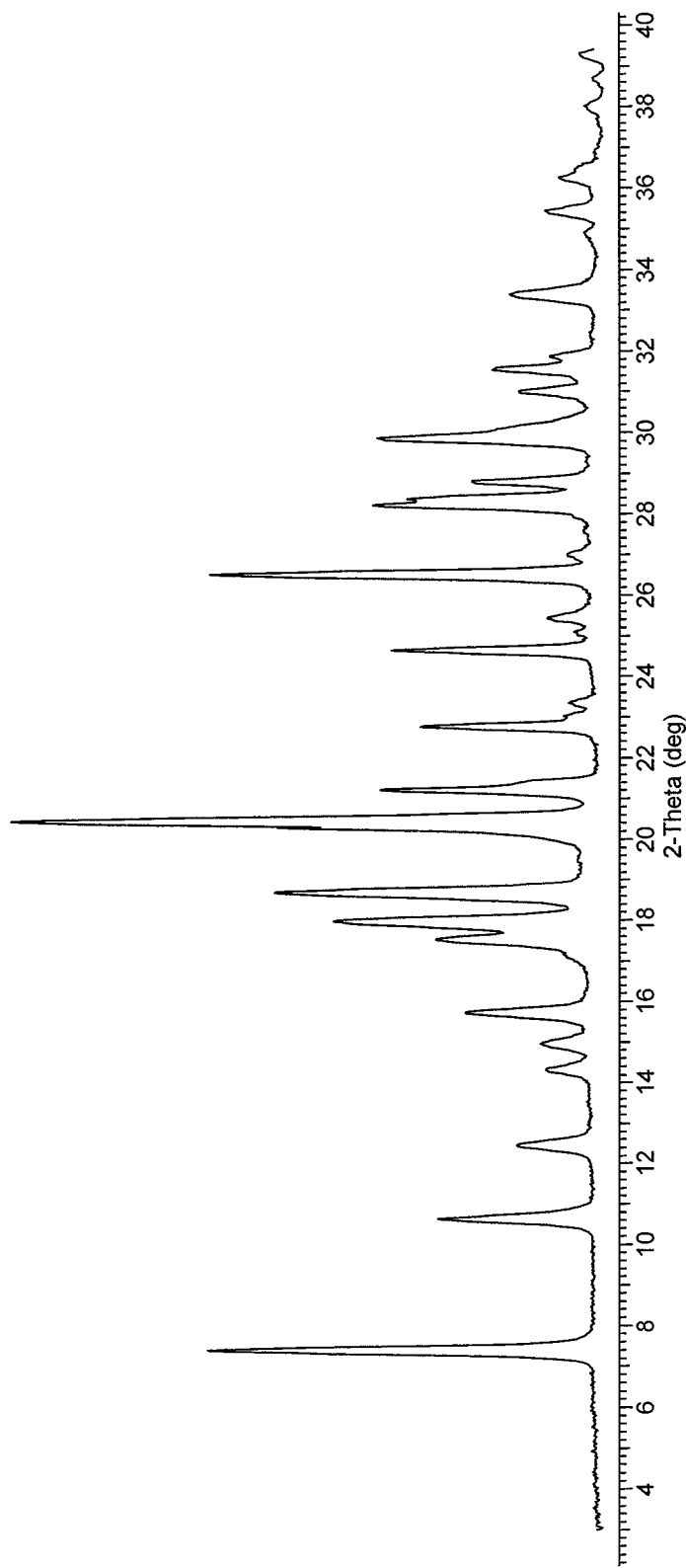
FIG. 2 shows the X-ray powder diffraction pattern of nitrate salt.

The following Examples illustrate the invention without limiting its scope, though they also form specific embodiments of the invention.

Abbreviations used:
IPA isopropyl alcohol
RH relative humidity
XRDP X-ray powder diffraction pattern If not mentioned otherwise, all reactions are carried out at room temperature (21 to 24° C., e.g. 23° C.).

Example 1

Phosphate salt of 4-(R)-(6,7-dihydro-5H-pyrrolo[1,2-c]imidazol-5-yl)-3-fluoro-benzonitrile (Form A)

2 g of free base was dissolved in a 40 ml ethanol and 1 equivalent phosphoric acid was added over the course of several minutes. After addition, solids were collected by filtration. The solids were dried at 22° C. under nitrogen flow. About 1.8 g were collected.

The molar ratio of phosphate to 4-(R)-(6,7-dihydro-5H-pyrrolo[1,2-c]imidazol-5-yl)-3-fluoro-benzonitrile in the obtained salt is 1:1.

In water, the phosphate salt was soluble at the 0.1% target concentration and stable for 2 days at 50° C. The free base remained largely insoluble. It converted from a free flowing solid into an oily material within a short time after contact with water, and remained as such for the 2 day period at 50° C.

Hygroscopicity

Sorption/desorption isotherms were measured using the VTI 100 humidity microbalance (VTI Corporation, Hialeah, Fla., USA). Measurements were carried out at 25° C. Samples were dried under $N_2$ flow at 25° C.

The hygroscopicity of the phosphate salt was found to be only 0% water uptake at 5% RH and 0.9% water uptake at 75% relative humidity.

Determination of Solubility

Excess solids were equilibrated in each solvent for over 24 hours at 25° C.±0.1. Concentration in supernatant was measured by gravimetry for organic solvents and by HPLC from aqueous solvents and propylene glycol.

The following results were obtained for the phosphate salt in comparison with the free base:

TABLE 1-1

| | Solubility profile (mg/ml) | |
| --- | --- | --- |
| Solvent | Free base | Phosphate salt |
| pH 1 | >50 | >50 |
| pH 6.8 | 28.6 | >50 |
| Water | 7.2 | >50 |
| Ethanol | >50 | 5.8 |
| Acetone | >50 | 1.5 |
| Propylene glycol | 34.4 | 1.5 |
| Ethyl Acetate | >50 | n.d. |

This shows that the solubility of the phosphate salt is comparably low in non-aqueous solvents which are thus anti-solvents for the salt, thus making it possible to achieve good precipitation and thus good yields and good purity. On the other hand, the solubility in water is better than that for the free base which is advantageous for providing oral or parenteral formulations.

The melting point was determined by TG/DTA as described above and was determined to be 210.2° C.

Determination of the XRDP:

TABLE 1-2

| Parameters and device used: | |
| --- | --- |
| XRPD-method | |
| Instrument | D8; Bruker (Karlsruhe, Germany) |
| Irradiation | CuKα (40 kV, 40 mA) |
| Scan time | 4 minutes (2 minutes per frame) |
| Scan range | 3°-40° (2 theta value) |

The XRDP obtained for this first phosphate form (Form A) is shown in FIG. 1-A.

The following table shows the corresponding angle of refraction 2-Theta values (in degrees [°]) for the important peaks:

TABLE 1-3

| Form A Measured 2-Theta (degrees) | Peak |
|---|---|
| 6.0 | 1 |
| 10.0 | 2 |
| 12.1 | 3 |
| 12.9 | 4 |
| 14.0 | 5 |
| 14.5 | 6 |
| 15.5 | 7 |
| 16.0 | 8 |
| 16.3 | 9 |
| 17.5 | 10 |
| 18.2 | 11 |
| 18.4 | 12 |
| 19.7 | 13 |
| 20.4 | 14 |
| 22.1 | 15 |
| 24.3 | 16 |
| 29.2 | 17 |

Example 2

Nitrate salt of 4-(R)-(6,7-dihydro-5H-pyrrolo[1,2-c]imidazol-5-yl)-3-fluoro-benzonitrile 2 g of 4-(R)-6,7-dihydro-5H-pyrrolo[1,2-c]imidazol-5-yl-3-fluoro-benzonitrile free base was dissolved in 40 ml ethanol and 1 equivalent nitric acid (same molar amounts as molar amount of free base) was added over the course of several minutes. After addition, solids were collected by filtration. The sample was dried at 21° C. to 23° C. by dry nitrogen flow. The amount recovered was 1.7 g.

The resulting 4-(R)-(6,7-dihydro-5H-pyrrolo[1,2-c]imidazol-5-yl)-3-fluoro-benzonitrile nitrate salt has a 1:1 molar ratio of base to chloride. It shows the XRPD represented in FIG. 2.

The hygroscopicity (measured under the conditions mentioned in Example 1) of the nitrate salt of 4-(R)-(6,7-dihydro-5H-pyrrolo[1,2-c]imidazol-5-yl)-3-fluoro-benzonitrile was found to be 0% water uptake at 5% RH and 0.2% at 75% RH.

In water, the nitrate salt was soluble at the 0.1% target concentration and stable for 2 days at 50° C. The free base remained largely insoluble. It converted from a free flowing solid into an oily material within a short time after contact with water, and remained as such for the 2 day period at 50° C.

Solubility was determined as shown for Example 1 and the following results were obtained:

TABLE 2-2

| | Solubility profile (mg/ml) | |
|---|---|---|
| Solvent | Free base | nitrate salt |
| pH 1 | >50 | >50 |
| pH 6.8 | 28.6 | 21.8 |
| Water | 7.2 | 38.2 |
| Ethanol | >50 | 4.2 |
| Acetone | >50 | 2.8 |
| Propylene glycol | 34.4 | 13.0 |
| Ethyl Acetate | >50 | 1.5 |

Using the TG/DCA method described above, the melting point of the nitrate was determined to be between 160 and 163° C.

The following angle of refraction peaks (2 Theta in degrees) are found in the XRPD (using the method described in Example 1), also providing their approximate intensity:

TABLE 2-2

| No. | 2 Theta | Intensity |
|---|---|---|
| 1 | 7.4 | 93 |
| 2 | 10.6 | 41 |
| 3 | 12.5 | 23 |
| 4 | 15.0 | 18 |
| 5 | 15.7 | 35 |
| 6 | 17.5 | 42 |
| 7 | 18.0 | 64 |
| 8 | 18.7 | 78 |
| 9 | 20.4 | 137 |
| 10 | 21.2 | 54 |
| 11 | 22.8 | 45 |
| 12 | 24.6 | 51 |
| 13 | 26.5 | 92 |
| 14 | 28.2 | 56 |
| 15 | 28.8 | 33 |
| 16 | 29.9 | 55 |
| 17 | 31.0 | 23 |
| 18 | 31.5 | 29 |

Example 3

Further forms B to H of 4-(R)-(6,7-dihydro-5H-pyrrolo[1,2-c]imidazol-5-yl)-3-fluoro-benzonitrile phosphate salt The following salt modifications B to H were obtained as described below:

Preparation of Phosphate Salt Modification B

Form A of 4-(R)-(6,7-dihydro-5H-pyrrolo[1,2-c]imidazol-5-yl)-3-fluoro-benzonitrile phosphate salt was equilibrated in IPA for 72 hours at 50° C. Sample was collected by filtration and allowed to air dry. A melting temperature of form B of 209.0° C. was determined by TG/DTA.

Preparation of Phosphate Salt Modification C 30 mg of 4-(R)-(6,7-dihydro-5H-pyrrolo[1,2-c]imidazol-5-yl)-3-fluoro-benzonitrile phosphate salt was dissolved in water at high concentration then chilled to 5° C. Ethanol was added to precipitate form C. Sample was collected by filtration and allowed to air dry. A melting temperature of form C of 206.4° C. was determined by TG/DTA.

Preparation of Phosphate Salt Modification D 30 mg of 4-(R)-(6,7-dihydro-5H-pyrrolo[1,2-c]imidazol-5-yl)-3-fluoro-benzonitrile phosphate salt was dissolved in methanol at 50° C. and form D is precipitated by the addition of acetone. Sample was collected by filtration and allowed to air dry. A melting temperature of form D of 210.8° C. was determined by TG/DTA.

Preparation of Phosphate Salt Modification E 20 mg of 4-(R)-(6,7-dihydro-5H-pyrrolo[1,2-c]imidazol-5-yl)-3-fluoro-benzonitrile free base was dissolved in 2-propanol/water solution (4:1) at room temperature. An equal molar amount of phosphoric acid was added to yield form E. Sample was collected by filtration and allowed to air dry. A melting temperature of form E of 199.2° C. was determined by TG/DTA.

Preparation of Phosphate Salt Modification F 20 mg of 4-(R)-(6,7-dihydro-5H-pyrrolo[1,2-c]imidazol-5-yl)-3-fluoro-benzonitrile free base was dissolved in methyl i-butyl ketone at (4:1) at 50° C. An equal molar amount of phosphoric acid was added to yield form F. Sample was collected by filtration and allowed to air dry. A melting temperature of form F of 201.1° C. was determined by TG/DTA.

Preparation of Phosphate Salt Modification G 20 mg 4-(R)-(6,7-dihydro-5H-pyrrolo[1,2-c]imidazol-5-yl)-3-fluoro-benzonitrile free base was dissolved in methanol (+20% water) at 5° C. An equal molar amount of phosphoric acid was added to yield form G. Sample was collected by filtration and allowed to air dry. A melting temperature of form G of 170.8° C. was determined by TG/DTA.

Preparation of Phosphate Salt Modification H 20 mg 4-(R)-(6,7-dihydro-5H-pyrrolo[1,2-c]imidazol-5-yl)-3-fluoro-benzonitrile free base was dissolved in ethanol (+20% water) at 50° C. An equal molar amount of phosphoric acid was added to yield form H after the solution is chilled to room temperature. Sample was collected by filtration and allowed to air dry. A melting temperature of form H of 208.0° C. was determined by TG/DTA.

The following Table 3-1 shows the angle of refraction 2-Theta values (in degrees) for the XRDPs of FIG. 1-A to 1-H for Forms A to G in comparison to those for Form A, with characteristic peaks for each form in comparison to Form A being underlined:

TABLE 3-1

| 2-Theta | A | B | F | C | D | E | G | H |
|---|---|---|---|---|---|---|---|---|
| | | | Measured Relative intensity (I %) | | | | | |
| 6.0 | 100 | 6.0 | 6.0 | 6.0 | 6.2 | 6.4 | 6.0 | 6.0 |
| 10.0 | 11 | 9.8 | 10.0 | 10.0 | 10.0 | 10.3 | | 10.2 |
| 12.1 | 14 | 11.8 | 12.1 | 11.9 | 12.4 | 12.1 | 12.1 | 12.1 |
| | | 12.7 | | | | | | |
| 12.9 | 21 | 12.9 | 12.9 | 12.9 | 12.9 | 12.9 | 13.1 | 13.1 |
| | | | 13.8 | | 13.3 | | | |
| 14.0 | 10 | 14.0 | 14.0 | 14.0 | | 13.3 | 14.0 | 14.0 |
| 14.5 | 12 | 14.3 | | 14.5 | 14.8 | 14.5 | 14.5 | 14.5 |
| 15.5 | 18 | 15.2 | 15.5 | 15.5 | 15.5 | 15.2 | 15.5 | 15.5 |
| 16.0 | 17 | 16.0 | 16.0 | 16.0 | 16.0 | 16.0 | 15.8 | 16.2 |
| 16.3 | 20 | 16.3 | 16.6 | 16.3 | 16.6 | 16.8 | 16.3 | 16.5 |
| 17.5 | 10 | 17.5 | 17.5 | 17.8 | 17.5 | 17.5 | 17.5 | 17.5 |
| 18.2 | 13 | 18.0 | 18.2 | 18.2 | 18.2 | 18.2 | 18.2 | 18.2 |
| 18.4 | 12 | 18.4 | 18.4 | 18.4 | 18.4 | 18.4 | 18.4 | 18.4 |
| | | 19.3 | 19.1 | 19.3 | 19.3 | 19.3 | 19.3 | 19.3 |
| 19.7 | 59 | 19.7 | 19.7 | 19.7 | 19.7 | 19.7 | 19.7 | 19.7 |
| 20.4 | 20 | 20.1 | 20.1 | 20.1 | 20.2 | 20.1 | 20.1 | 20.1 |
| 22.1 | 44 | 22.1 | 22.1 | 22.1 | 22.1 | 22.1 | 22.1 | 22.2 |
| 24.3 | 26 | 24.3 | 24.3 | 24.3 | 24.3 | 24.3 | 24.3 | 24.3 |
| 29.2 | 23 | 29.2 | 29.2 | 29.2 | 29.2 | 29.2 | 29.2 | 29.5 |

Thus it can be shown that in addition to Form A (Example 1) further polymorphs (forms) of Compound A phosphate salt can be found.

Comparison Example

HCl salt of 4-(R)-(6,7-dihydro-5H-pyrrolo[1,2-c]imidazol-5-yl)-3-fluoro-benzonitrile 2 g of 4-(R)-(6,7-dihydro-5H-pyrrolo[1,2-c]imidazol-5-yl)-3-fluoro-benzonitrile free base was dissolved in 40 ml ethanol and 1 equivalent HCl (equal molar amount of HCl to the molar amount of the free base) was added over the course of several minutes. Since the system did not produce crystallization, the solvent was evaporated. The solids were suspended in methyl tertbutyl ether for 2 hours at room temperature. The solids were collected by filtration. The solids were dried at 22° C. under nitrogen flow. About 1.6 g were collected.

Figure 3:
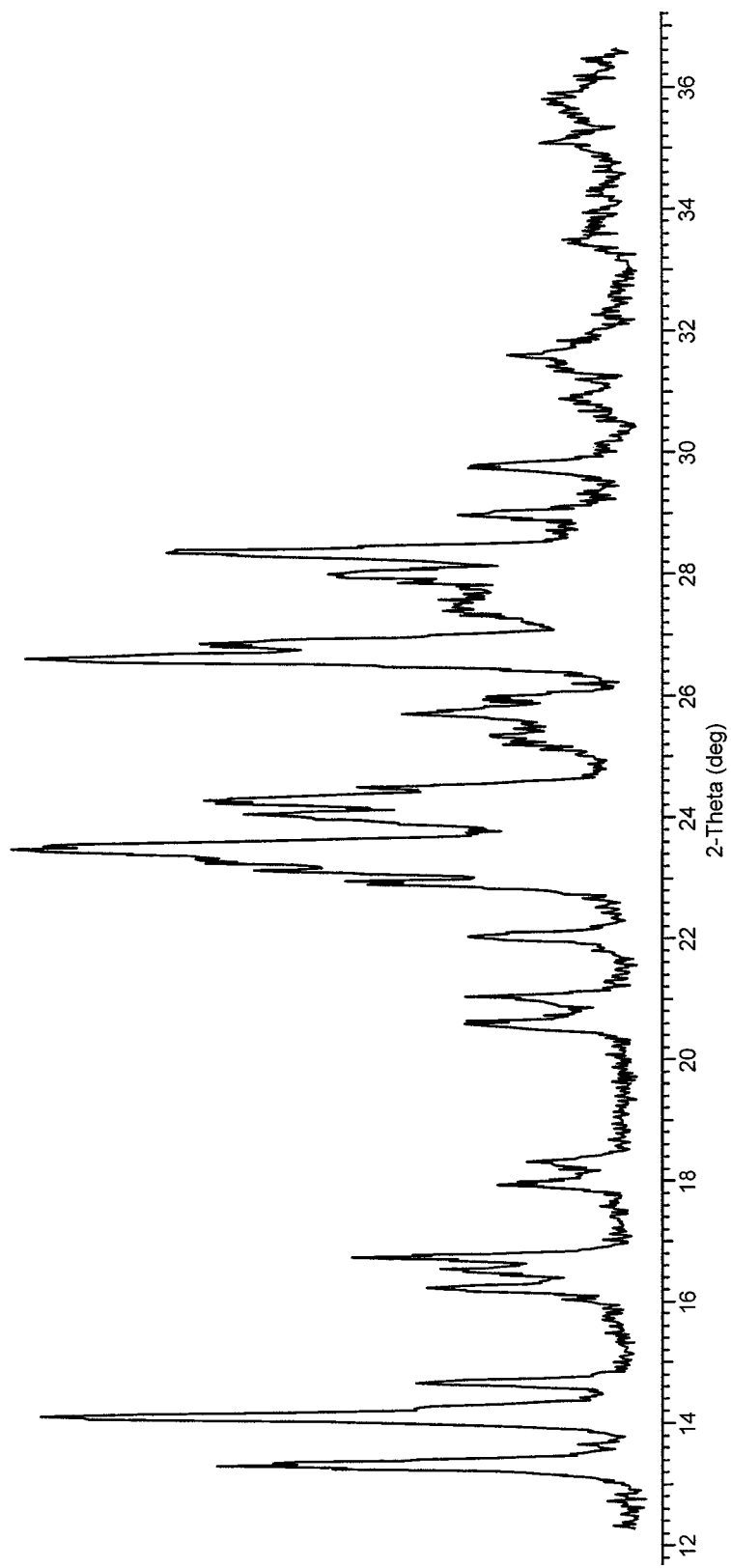
FIG. 3 shows the X-ray powder diffraction pattern of chloride salt.

The resulting 4-(R)-(6,7-dihydro-5H-pyrrolo[1,2-c]imidazol-5-yl)-3-fluoro-benzonitrile HCl salt has a 1:1 molar ratio of base to chloride. It showed the XRPD shown in FIG. 3.

The following peaks (in 2 Theta) were found in the XRPD (using the method described in Example 1):7

TABLE

| Comparison-1 | | |
|---|---|---|
| No. | Position | Intensity |
| 1 | 13.3 | 36 |
| 2 | 14.1 | 51 |
| 3 | 14.7 | 19 |
| 4 | 16.2 | 18 |
| 5 | 16.5 | 17 |
| 6 | 16.7 | 24 |
| 7 | 20.6 | 15 |
| 8 | 21.0 | 15 |
| 9 | 22.0 | 14 |
| 10 | 23.0 | 25 |
| 11 | 23.1 | 32 |
| 12 | 23.5 | 53 |
| 13 | 24.1 | 33 |
| 14 | 24.3 | 37 |
| 15 | 24.5 | 24 |
| 16 | 25.7 | 20 |
| 17 | 25.9 | 13 |
| 18 | 26.6 | 52 |
| 19 | 26.9 | 37 |
| 20 | 27.6 | 17 |
| 21 | 28.0 | 26 |
| 22 | 28.4 | 40 |
| 23 | 29.0 | 15 |
| 24 | 29.7 | 14 |

In contrast to both the phosphate and the nitrate salts, the HCl salt showed excessive hygroscopicity, as is shown in the following table:

| Moisture gain (%) comparison between forms (r.h. = relative humidity) | | | | |
|---|---|---|---|---|
| r.h. % | free base | Nitrate | Phosphate | HCl |
| 0 | 0.0 | 0.0 | 0.0 | 0.0 |
| 5 | 0.0 | 0.0 | 0.0 | 0.0 |
| 25 | 0.1 | 0.1 | 0.1 | 0.5 |
| 50 | 0.2 | 0.2 | 0.1 | 0.2 |
| 75 | 0.3 | 0.2 | 0.2 | 0.2 |
| 85 | 0.5 | 0.2 | 0.3 | 3.3 |
| 95 | 1.0 | 0.2 | 0.8 | 23.6 |

It will be apparent to those skilled in the art, that many modifications, both to materials, and methods, may be practiced with out departing from the purpose and interest of this invention.

The invention claimed is:
1. A nitrate salt of 4-(R)-6,7-dihydro-5H-pyrrolo[1,2-c]imidazol-5-yl-3-fluoro-benzonitrile.

* * * * *